United States Patent
Fontenot

(10) Patent No.: US 6,716,180 B2
(45) Date of Patent: Apr. 6, 2004

(54) OVER THE WIRE BREAST BIOPSY SYSTEM

(76) Inventor: Mark G. Fontenot, 229 Marilyn Dr., Lafayette, LA (US) 70503

( * ) Notice: Subject to any disclaimer, the term of this patent is extended or adjusted under 35 U.S.C. 154(b) by 0 days.

(21) Appl. No.: 10/099,311

(22) Filed: Mar. 12, 2002

(65) Prior Publication Data

US 2002/0095101 A1 Jul. 18, 2002

Related U.S. Application Data

(63) Continuation of application No. PCT/US00/25101, filed on Sep. 13, 2000.
(60) Provisional application No. 60/153,807, filed on Sep. 14, 1999.

(51) Int. Cl.[7] .............................................. A61B 10/00
(52) U.S. Cl. ...................................................... 600/567
(58) Field of Search .................................. 600/567, 564, 600/565, 566; 606/45, 46, 41, 167, 170; 604/21

(56) References Cited

U.S. PATENT DOCUMENTS

| | | |
|---|---|---|
| 5,810,806 A | 9/1998 | Ritchart et al. |
| 5,848,978 A | 12/1998 | Cecchi |

*Primary Examiner*—Max F. Hindenburg
*Assistant Examiner*—Brian Szmal
(74) *Attorney, Agent, or Firm*—Townsend and Townsend and Crew LLP

(57) ABSTRACT

Systems comprising a wire and an excision instrument particularly intended for breast biopsy are provided. The excision instrument has a fixed or attachable blade for taking a sample.

5 Claims, 6 Drawing Sheets

FIG. 1 (a)
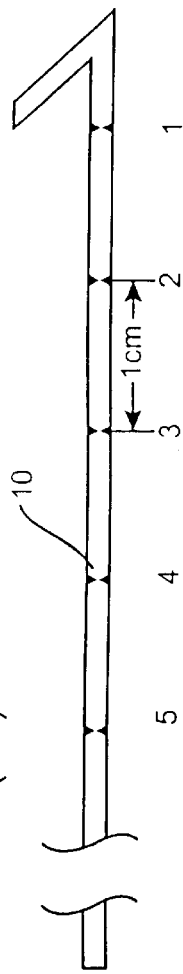
FIG. 1 (aa)
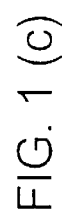
FIG. 1 (c)
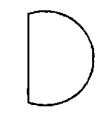
FIG. 1 (e)
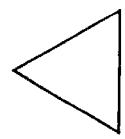
FIG. 1 (b)
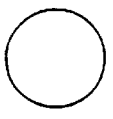
FIG. 1 (d)

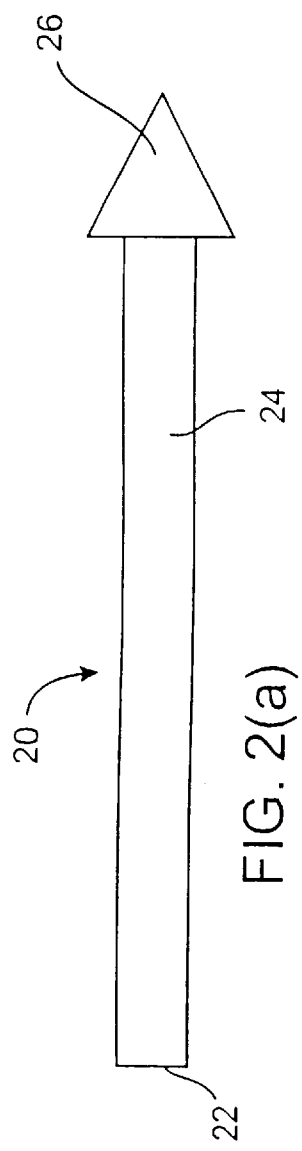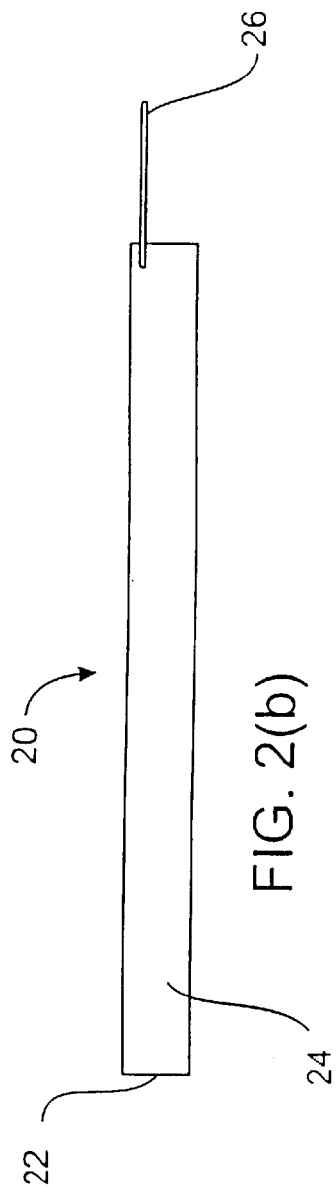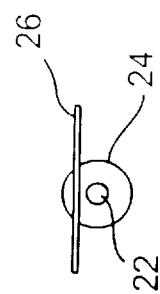
FIG. 2(a)
FIG. 2(b)
FIG. 2(c)

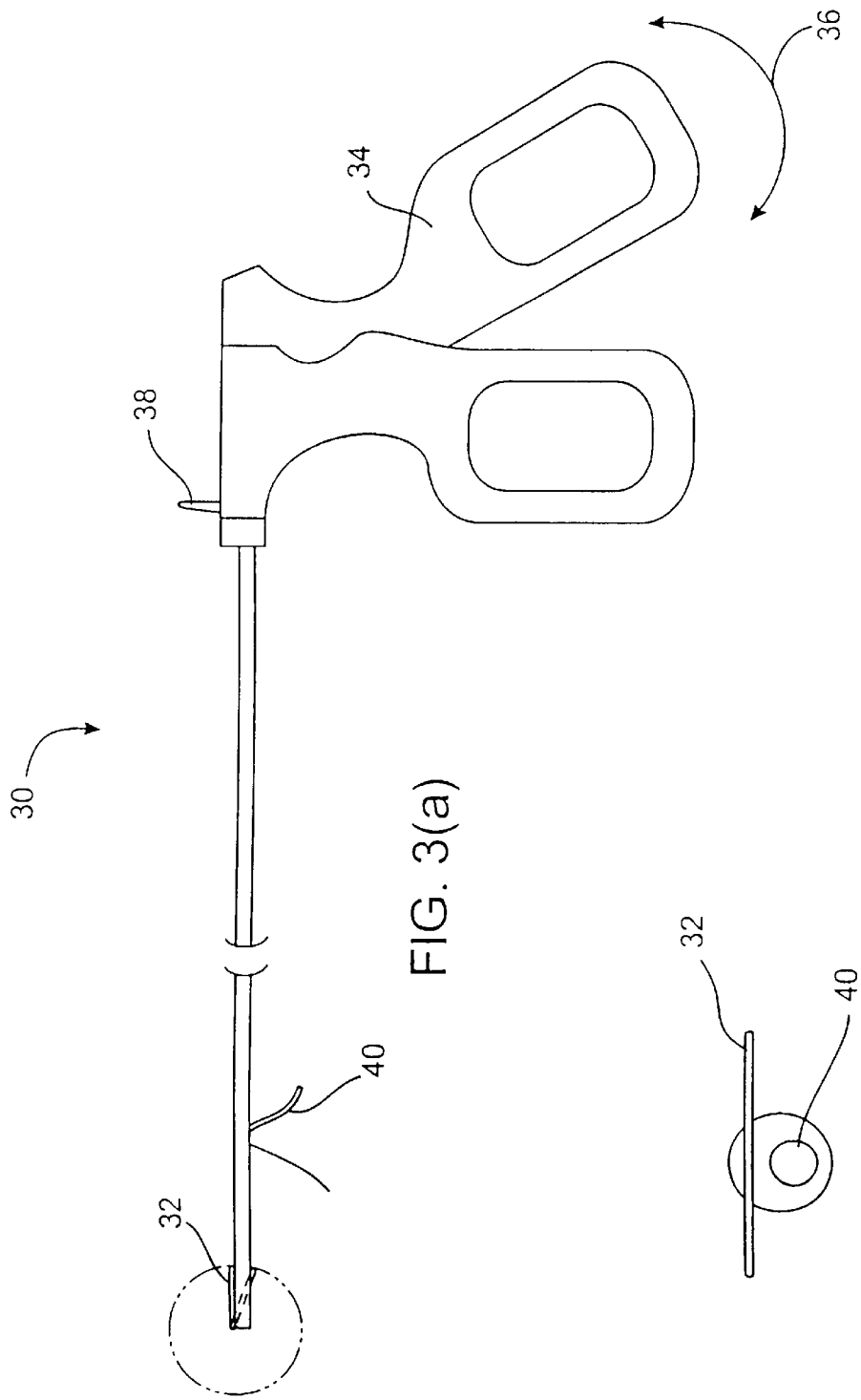

OVER THE WIRE BREAST BIOPSY SYSTEM

CROSS-REFERENCES TO RELATED APPLICATIONS

This application is a continuation of PCT/US00/25101, filed on Sep. 13, 2000, which claimed the benefit of provisional application No. 60/153,807, filed on Sep. 14, 1999, the full disclosures of which are incorporated herein by reference.

BACKGROUND OF THE INVENTION

1. Field of the Invention

The present invention relates to method and devices for removing a predetermined amount of breast tissue for the purposes of treatment and/or microscopic examination.

2. Description of the Background Art

Wire needle localization (WNL) is a surgical technique frequently invoked by surgeons to biopsy lesions in the breast discovered as a result of mammography or other breast screening methods. Patients undergoing WNL are placed on a radiographic table usually located in the radiology suite. The breast is placed between two compression plates, arranged moveably in relation to one another, for fixing the breast therebetween. The compression plates have through holes which permit the introduction of a biopsy needle into the breast and proximate to the breast lesion under radiographic guidance. Once the needle is placed in the desired position in the breast, a thin, stiff wire with a distal retaining hook is inserted through the lumen of the needle. As the wire emerges from the distal aspect of the needle, the distal hook of the wire engages the breast tissue proximate to the breast lesion. The needle is withdrawn leaving the hook wire proximate to the lesion. The position of the wire relative to the lesion is verified radiographically. Radiographic views of the wire in the breast are taken and brought to the operating so as to allow the surgeon to plan the surgical biopsy procedure.

The patient is transferred to the operating room. The surgeon plans his approach to surgically retrieving and adequate tissue specimen after physically examining and reviewing the radiographs of the breast with the wire placed in proximity to the breast lesion. The wire serves as a marker which can be palpated by the surgeon at the time of and during surgery which serves as a marker during surgery. Local anesthetic is administered in and around the proposed surgical area. An incision is made and the surgeon dissects around the wire. During the dissection, the surgeon continuously palpates the location of the wire in order to orient the dissection and determine that amount of tissue to be harvested or biopsied.

The surgical objective of the biopsy is to remove an adequate tissue sample such that the wire and the lesion are at the center of the sample surrounded by an adequate margin thickness of normal breast tissue. In other words, the ideal specimen can be compared to a peach wherein the pit or seed is analogous to the lesion and the pulp completely surrounding the seed is analogous to normal tissue.

WNL is a useful technique for surgically excising an amount of tissue adjacent to a palpable landmark such as a wire. However, the surgeon is often confronted with making an intraoperative estimation of the amount of tissue to be biopsied by the radiograph appearance of the lesion and its relative location to the wire as well as intraoperative findings and surgical approach to the wire. In addition, instrumentation or techniques for open surgical breast biopsies that remove a predetermined amount of breast tissue are not currently known or practiced.

BRIEF SUMMARY OF THE INVENTION

Objects of the Invention. It is an object of the present invention to provide method and devices which allows surgeons to remove a predetermined amount of breast tissue based on radiographic findings of the lesion to be biopsied.

It is another object of the present invention to provide an over the wire device to make and incision and dissect tissue along a path determined by the placement of a scalpel over a wire.

It is still another object of the invention to provide an over the wire tissue harvester device that uses energy to cut a predetermined amount of tissue for the purposes of treatment or examination.

Summary of the Invention. The present invention relates to surgically removing a predetermined amount of breast tissue for treatment and/or microscopic examination. More particularly, the invention describes a method employing apparatuses including a small, stiff guide wire placed adjacent to the lesion to be biopsied, an over the wire scalpel, and an over the wire tissue harvester. The method and associated devices employed in the invention consists of four steps, namely (1) placement of the wire proximate to the breast lesion under radiographic guidance, (2) using a graduate template and a radiograph of the wire placed in the breast proximate to the breast lesion to be removed, measurements of the proposed breast tissue to be surgically removed are made, (3) from these measurements, selection of the appropriate scalpel is made, then placed over the wire and advanced resulting in a skin incision, creating access to the lesion, and working space to the desired level within the breast, and (4) from the incision and the measurements, the appropriate tissue harvester is selected and advanced over the wire to the desired position and secured, then the hoop is actuated simultaneous to the activation of electrical energy through the hoop and a predetermined amount of breast tissue is swathed by the action of the hoop rotating about its pinned position at the most distal aspect of the tissue harvester. In one embodiment a trailing bag can be attached to the hoop to enclosed the breast tissue to be removed as the hoop traverses through the breast tissue. In yet another embodiment, the wire is scored so the surgical position can be related to the radiographic position.

BRIEF DESCRIPTION OF THE DRAWINGS

FIGS. 1(*a*) and (*aa*) are side elevations of a wire without and with graduated markings, and FIGS. 1(*b*)–1(*e*) are end views of the different cross-sectional types of wire: triangular (b), square (c), round (d), and half round (e). The wire is typically fabricated from stainless steel wire.

FIGS. 2(*a*)–(*c*) are top, side, and end views, respectively, of an over-the-wire scalpel 20 having a lumen 22 therebetween. The over the wire scalpel consists of a plastic or metal guide handle 24 with a lumen traversing the entire length of the handle and open at both ends. A triangular shaped scalpel blade 26 can be fixed or reversibly coupled to the distal end. The scalpel blade is fabricated from stainless steel and the leading edges of the blade are cutting. The shape of the scalpel is not limited to being triangular but can take on other shapes such as half round, oval, and other shapes with a leading edge that is honed to cut tissue.

FIGS. 3(*a*) and (*b*) are side and end views of the over a wire tissue harvester 30. A hoop 32 is actuated by moving the finger grips 34 to and fro as indicated by arrow 36. Electrical energy is delivered to the hoop by coupling an electrical energy source to a coupler 38. A lumen 40 in the distal third of the shaft allows the tissue harvester to be placed at or near the distal end of the wire by placing the proximal end of the wire into the lumen and advancing the tissue harvester into the proper position.

DETAILED DESCRIPTION OF THE INVENTION

Figure 4:
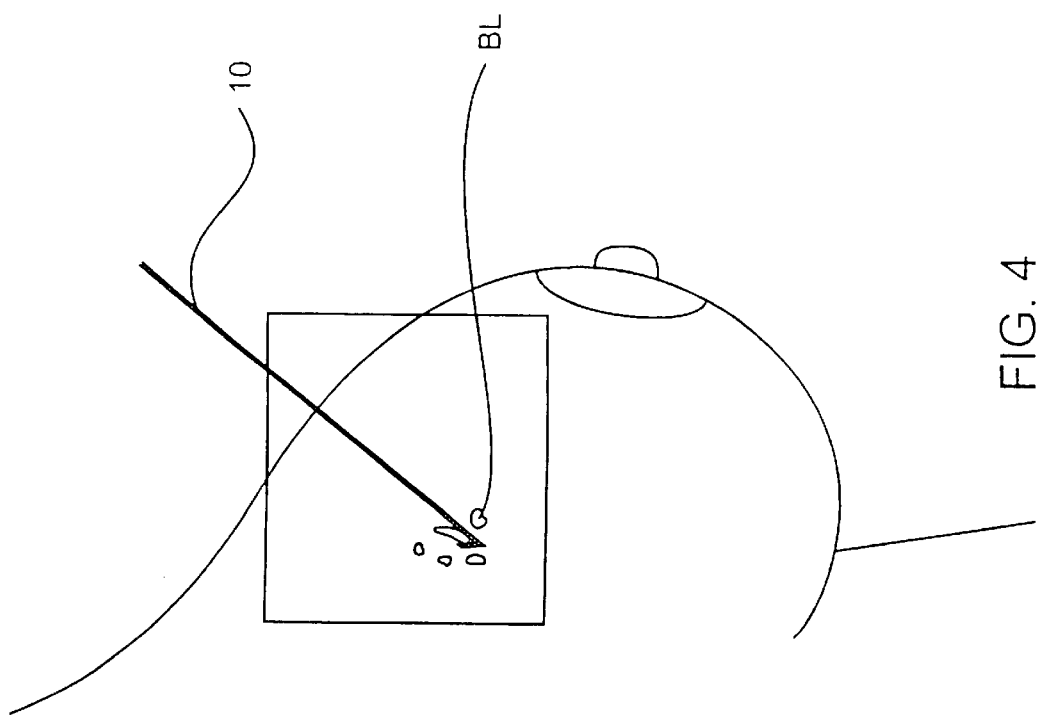
FIG. 4 is a schematic view showing the placement of the wire 10 adjacent to a breast lesion BL that is to be removed.
Figure 5A:
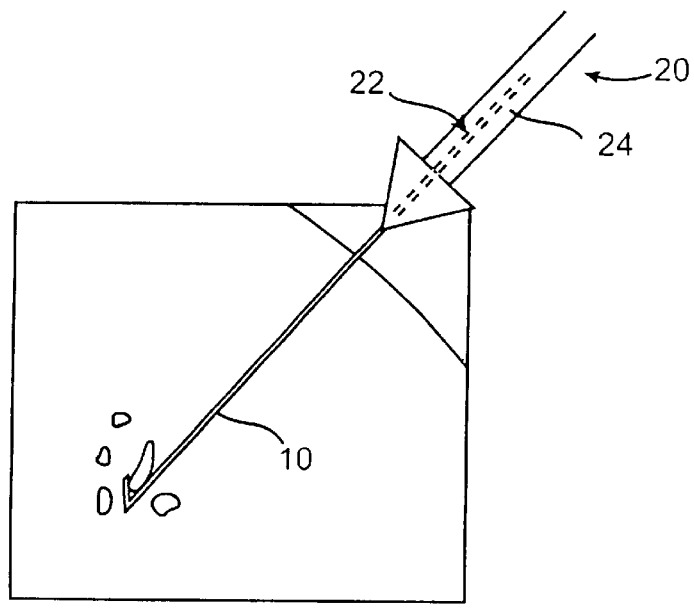
FIGS. 5(*a*)–(*d*) are schematic views showing a method and application for using the over the wire scalpel. The wire 10 is placed in the lumen 22 of the scalpel guide handle FIG. 5(*a*). The scalpel 26 is advanced to the distal end or near the distal end of the wire FIG. 5(*b*). The resulting incision I and dissection path DP facilitates placement of the over the wire tissue harvester and extraction route of the biopsied breast tissue. An indexed wire in the form of a square wire can be used to guide the scalpel FIG. 5(*c*). A round wire also can be used as shown in FIG. 5(*d*), however the round wire may allow twisting of the scalpel or the over the wire tissue harvester about the axis of the wire.
Figure 5B:
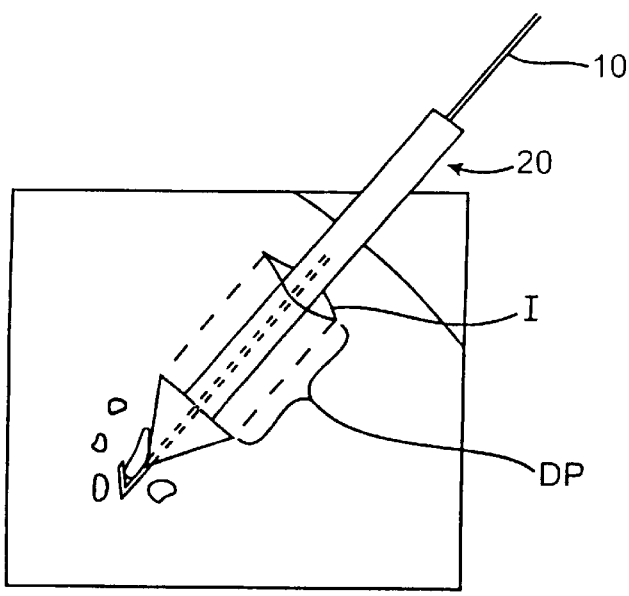
Figure 5C:
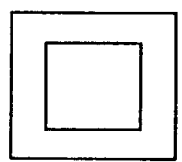
Figure 5D:
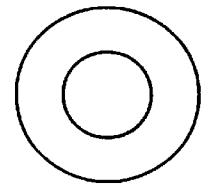

Referring to FIG. 4, the wire is placed proximate to area to be biopsied using standard radiographic techniques for the placement of a wire for wire localization procedures of breast lesions. The patient is brought to the operating room. Local anesthetic is administered at the proposed incision site and area to be biopsied. The surgeon reviews the preoperative radiographs showing the wire in proximate location to the breast lesion to be biopsied or removed. The area, including the proper amount of margin of breast tissue to be removed, is measured directly on the radiograph using a template for the over the wire scalpel and tissue harvester. From these measurements, the proper size over the wire scalpel is selected. For example, if the area to be biopsied is 1 cm and the required margin of tissue to be removed around the lesion is 1 cm, then a 3 cm scalpel would be the maximum size selected. When selecting the appropriate scalpel, it is typical to consider a 20% to 50% reduction in the size of the scalpel due to the elasticity of tissue. As such, the surgeon may select a 2.5 cm scalpel which is width of the blade.

Figure 6C:
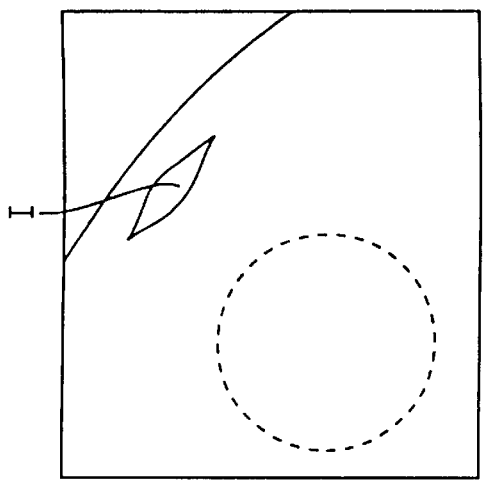
FIG. 6 is a schematic view showing a method using the over the wire tissue harvester 30. The wire 10 is placed in the lumen of the tissue harvester. The tissue harvester is positioned at or near the distal end of the wire 10. The hoop 32 of the harvester is actuated simultaneous to the activation of electrical energy through the hoop. The path traversed by the hoop P results in cylinder of tissue which is extracted through the incision site I, as shown in FIG. 6(*c*).
Figure 6B:
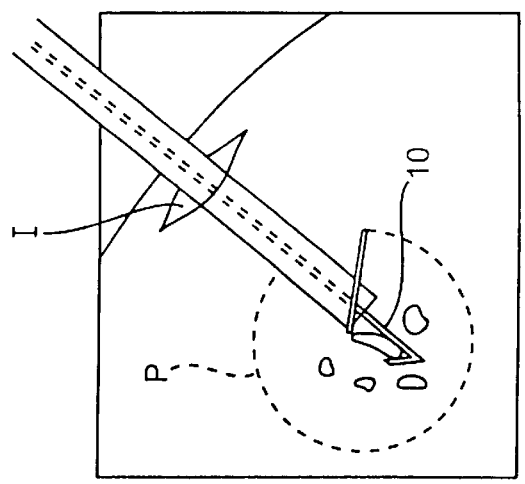
Figure 6A:
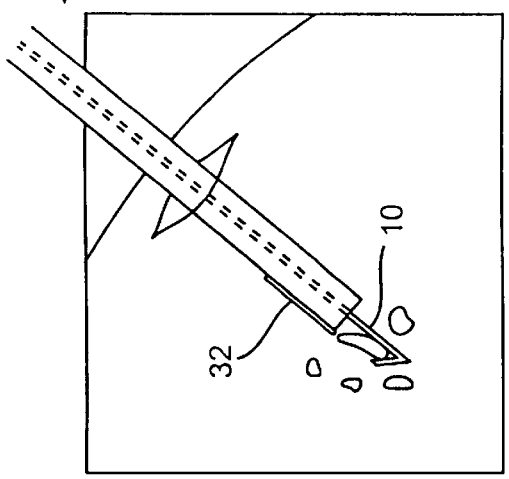

Referring to FIGS. 5 and 6, the proximal end of the wire is placed in the lumen of the scalpel guide handle beneath the blade (FIG. 5(*a*)). The width of the scalpel selected in this embodiment is 2.5 cm which is the width of the blade. The over the wire scalpel is advanced such that the blade incises the skin and underlying breast tissue as the scalpel traverses the wire (FIG. 5(*b*)). The over the wire scalpel can be advanced near or at the distal end of the wire or to a desired position. When the desired position of the scalpel is reached along the length of the wire, it is withdrawn. Commonly used hemostatic techniques can be used to control bleeding. The advancement of the over the wire scalpel into the breast tissue creates working space that will allow the placement of the tissue harvest as well as an adequate retrieval route for the biopsied breast tissue.

Referring to FIG. 6, the appropriate over the wire tissue harvester is introduced into the surgical site. The friction grip is tightened and the tissue harvester is secured to the wire in the desired positioned. Specifically, in this embodiment, a 3 cm tissue harvester is used which is the width of the hoop that corresponds to the measured amount of breast tissue to be removed (see FIG. 3(*b*)). The proximal end of the wire introduced into the distal end of the tissue harvester lumen. The over the wire tissue harvester is advanced to the desired position relative to the distal end of the wire (FIG. 6(*a*)). The hoop is actuated simultaneous to the activation of electrical energy through the hoop. The tissue is cut and cauterized as the hoop traverses through the breast tissue (FIG. 6(*b*)). When completed, the lateral tissue tags are cut or cauterized using a typical scalpel or bovie, respectively. The over the wire harvester is removed. A pair of graspers clamps the biopsied tissue and extract through the incision site (FIG. 6(*c*)).

In another embodiment of the over the wire tissue harvester, a plastic bag may be attached to the hoop and folded. As the hoop traverses the tissue, the bag deploys around the harvested tissue. The lateral tissue tags are cut or cauterized. Thus, the specimen is contained within the bag and removed when the over the wire tissue harvester as it is retracted from the surgical site. In yet another embodiment, small scores are placed on the wire and are visible on a radiograph. These scores act as depth measurement that can related the desired position intraoperatively to the radiograph. These scores also help to assess the amount of resulting magnification that occurs during radiographic imaging.

What is claimed is:

1. A tissue biopsy system comprising:
   a wire having an anchor at a distal end thereof;
   an excision instrument having a fixed cutting blade adapted to travel over the wire to a tissue region marked by the anchor; and
   an over-the-wire tissue harvester having a rotating hoop.

2. A system as in claim 1, wherein the cutting blade of the excision instrument is a triangular blade.

3. A system as in claim 2, wherein the hoop of the tissue harvester is adapted to be activated with electrical energy.

4. A system as in claim 1, wherein the wire is scored to allow position determination under radiographic imaging.

5. A method for biopsying breast tissue, said method comprising:
   placing a wire at a target location in the breast tissue under radiographic guidance;
   measuring the depth of the target location using a template;
   selecting an excision instrument based on the measurement;
   advancing the excision instrument over the wire to form a path to the biopsy site;
   withdrawing the excision instrument through the path;
   advancing a tissue harvester over the wire;
   rotating a hoop on the tissue harvester to excise a cylinder of tissue at the biopsy site;
   withdrawing the tissue harvester from the path; and
   removing the cylinder of tissue from the biopsy site.

* * * * *